US 8,494,787 B2

(12) United States Patent
McLeod

(10) Patent No.: US 8,494,787 B2
(45) Date of Patent: Jul. 23, 2013

(54) MAGNETIC INK FOR MARKING DEFECTIVE PARTS OR ASSEMBLIES DURING MANUFACTURING

(75) Inventor: Scot McLeod, San Diego, CA (US)

(73) Assignee: Quidel Corporation, San Diego, CA (US)

( * ) Notice: Subject to any disclaimer, the term of this patent is extended or adjusted under 35 U.S.C. 154(b) by 111 days.

(21) Appl. No.: 12/077,885

(22) Filed: Mar. 21, 2008

(65) Prior Publication Data
US 2008/0262644 A1    Oct. 23, 2008

Related U.S. Application Data

(60) Provisional application No. 60/919,366, filed on Mar. 21, 2007.

(51) Int. Cl.
G01B 5/28    (2006.01)
(52) U.S. Cl.
USPC ............................................................ 702/35
(58) Field of Classification Search
USPC . 702/35; 156/64, 248; 700/222, 224; 101/35; 209/3.3, 33; 235/449; 436/174; 348/127; 114/356; 427/130; 429/127
See application file for complete search history.

(56) References Cited

U.S. PATENT DOCUMENTS

| | | | |
|---|---|---|---|
| 3,572,400 A | | 3/1971 | Casner et al. |
| 3,587,855 A | * | 6/1971 | Roy et al. ........................ 209/3.3 |
| 3,806,015 A | | 4/1974 | Kachioff et al. |
| 3,958,078 A | * | 5/1976 | Fowler et al. ................... 348/127 |
| 3,969,640 A | * | 7/1976 | Staudte .......................... 310/312 |
| 5,458,062 A | | 10/1995 | Goldberg et al. |
| 5,808,265 A | | 9/1998 | Cecil |
| 5,873,966 A | * | 2/1999 | Goldberg et al. ................ 156/64 |
| 6,352,497 B1 | | 3/2002 | Hensley et al. |
| 6,354,984 B1 | | 3/2002 | Hensley et al. |
| 6,624,540 B2 | | 9/2003 | Fukuda et al. |
| 6,856,859 B1 | * | 2/2005 | Bett et al. ........................ 700/222 |
| 7,255,273 B2 | * | 8/2007 | Rumsey ........................... 235/449 |
| 2004/0018422 A1 | * | 1/2004 | Islam et al. ...................... 429/127 |
| 2004/0142486 A1 | * | 7/2004 | Weselak et al. .................. 436/174 |
| 2004/0173109 A1 | * | 9/2004 | Sosin ................................. 101/35 |
| 2008/0060751 A1 | * | 3/2008 | Arrindell ........................ 156/248 |
| 2008/0193639 A1 | * | 8/2008 | Adams et al. .................. 427/130 |
| 2008/0236704 A1 | * | 10/2008 | Risi ................................ 144/356 |
| 2009/0000250 A1 | * | 1/2009 | Nilsson et al. .................. 53/396 |

FOREIGN PATENT DOCUMENTS

GB    2 363 252 A    12/2001
WO    WO 2006093447 A1 *    9/2006

OTHER PUBLICATIONS

International Search Report and Written Opinion for PCT application PCT/US2008/003756, search report dated Jun. 19, 2008, 11 pages (2008).

* cited by examiner

Primary Examiner — Jonathan C Teixeira Moffat
Assistant Examiner — Xiuquin Sun
(74) Attorney, Agent, or Firm — McDermott Will & Emery LLP

(57) ABSTRACT

Magnetic ink is used to mark defective parts or assemblies during manufacturing, thereby allowing the defective parts or assemblies to be detected in products following manufacturing, even if they are concealed or hidden in the final product. An example of such a defect-containing product is a laminated microfluidic device which contains a defective capillary.

8 Claims, No Drawings

MAGNETIC INK FOR MARKING DEFECTIVE PARTS OR ASSEMBLIES DURING MANUFACTURING

CROSS REFERENCE TO RELATED APPLICATIONS

The application claims the benefit of U.S. Provisional Application No. 60/919,366, filed Mar. 21, 2007, incorporated herein by reference in its entirety.

TECHNICAL FIELD

The methods relate to the use of magnetic ink for marking defective parts or assemblies during manufacturing, thereby allowing the defective parts or assemblies to be detected in products following manufacturing, even if concealed or hidden in the product. The methods are particularly useful in continuous manufacturing processes, such as reel-to-reel manufacturing, particularly, of laminated products.

BACKGROUND

Small electronics and other devices (or components thereof) have traditionally been manufactured and assembled on a loose-parts basis. However, even with high-speed equipment, handling every part individually was inefficient. These inefficient manufacturing methods are giving way to fully automated, hands-off manufacturing processes.

Among the new manufacturing methods is reel-to-reel processing, which uses a feed reel and a take-up reel to control a continuous, indexed carrier strip, to which components are attached for manipulation and assembly, e.g., at different stations along an assembly line. The continuous strip is automatically rewound on the take-up reel when a monitor senses sufficient slack between a station and the take-up reel. The carrier strip does may be a metal, composite, or polymer strip, including a wire or cable. The completed or assembled parts or precursors may be delivered to an end user or customers still on the take-up reel or removed from the carrier strip for packaging and delivery. Such manufacturing technology is particularly well suited for electronic components such as ICs, discrete electronic devices, DIP switches, and connectors as well as for laminated assay devices as described further herein.

Reel-to-reel manufacturing often takes well-established technologies and processes to higher levels of convenience and cost reduction. Among the advantages of reel-to-reel manufacturing are the automated handling of components, lower production costs, higher volume throughput, less process error (high repeatability and quality), and consistent part orientation for ease and speed of assembly.

Quality control in reel-to-reel manufacturing is paramount. Cameras are often used to inspect up to 100% of the individual strip-mounted products. The cameras may check the part surface, shape, position, dimensions, and/or the presence or absence of a critical feature. However, the ability to detect defects does not immediately translate into the ability to discard the defective assemblies of products. Interrupting reel-to-reel manufacturing to remove defective assemblies defeats the purpose of using the high speed manufacturing process; therefore, defective assemblies often remain on the strip, to be detected and isolated at the end of the manufacturing process. Unfortunately, some defect in an assembly may be difficult to detect in the finished product, particularly where the product consists of a number of layers or subassemblies that are hidden or even physically inaccessible in the final product or component of a product, such as, for example due to lamination of components. Index marks on the strip may assist in later identifying the defective parts to be discarded; however, such index marks must be reliable to avoid discarding good products and passing defective products to consumers. Moreover, where several parts align with the same index markers, numerous parts may have to be discarded to assure that the defective part is removed.

The need exists for a method for individually marking defective assemblies that are detected during manufacturing, such that the marking may be detected at a later stage of manufacturing, even if the marking is hidden within the assembly or product.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In one aspect, a method is provided for detecting a defective assembly in a final product of manufacture, the defect being identified during manufacturing, and the defective assembly being substantially concealed in the final product, the method comprising:

a) identifying a defect in an assembly during manufacturing;

b) marking the defective assembly with magnetic ink during manufacturing;

c) detecting the magnetic ink in a final product; and d) isolating the defective product so marked;

wherein the magnetic ink allows the detection of the defective assembly that is substantially concealed in a final product of manufacture.

In some embodiments, the final product of manufacture is a laminated device. In certain embodiments, the defect is in a layer of the laminated device, the layer being substantially concealed in the final product. In a particular embodiment, the defect is a defect in alignment or positioning of materials relative to one another and/or deposition of reagents on material components of a laminated device, particularly an assay device.

In some embodiments, manufacturing is performed using a reel-to-reel process. In some embodiments, the defect is identified using a camera to visually inspect the assembly during manufacturing. In particular embodiments, the marking is performed by spraying magnetic ink on the assembly.

In some embodiments, the marking is performed by spotting magnetic ink on the assembly.

In some embodiments, the final product of manufacture is an assay device.

In some embodiments, the assay device is a laminated test strip-based assay device.

In another aspect, a product of manufacture comprising a substantially concealed magnetic ink mark is provided.

In addition to the exemplary aspects and embodiments described above, further aspects and embodiments will become apparent by study of the following descriptions.

DETAILED DESCRIPTION

I. Definitions

As used herein, "defective" means flawed or imperfect such that a part or assembly is unsuitable or unacceptable for all or part of its intended purpose. Defective includes such terms as broken, scratched, warped, misaligned, inoperable, etc. A defect may be structural, functional, or aesthetic.

As used herein, "during manufacturing" means in the course of a continuous manufacturing process, such as a reel-to-reel operation or other assembly-line process, wherein the parts or assemblies are subjected to consecutive operations or procedures, typically with minimal delay between steps.

As used herein, "substantially concealed" with respect to a part or assembly of a final or intermediate product of a continuous manufacturing process refers to a part or assembly that is hidden or obscured in a final product such that visible marks made to the part or assembly would be difficult or impossible to detect in the final product. Substantially concealed encompasses entirely concealed, 99% concealed, 95% concealed, 90% concealed, or even 80% concealed, compared to the visibility or accessibility of the part or assembly prior to incorporation into the final product.

As used herein, a "final product of manufacture," or similar terms, refers to the end result of a continuous manufacturing process, for example, reel-to-reel manufacturing. A final product is the end result of substantially uninterrupted processing, as in the case of an assembly line. Where a final product requires a plurality of continuous manufacturing steps, or combines components from different continuous manufacturing steps, a final product of manufacture may refer to either or both each intermediate that results from one of the continuous manufacturing steps or, where the plurality of components are further combined via an automated continuous process, the resulting combined product.

As used herein, the term "assay device" refers to a device for performing an assay on a sample, preferably a biological sample, preferably to detect the presence, absence or quantity of a target substance within the sample. Examples of assay devices include but are not limited to lateral (or vertical) flow assay devices comprising a test strip comprising one or more porous materials that, when contacted with a sample, permit lateral (or vertical) flow of the sample within, across and/or on the test strip, the test strip further comprising reagents deposited on and/or within a portion of such porous materials such that flowing sample contacts said reagents resulting in reactions indicative of the presence, absence and/or quantity of the target substance. In some instances, for example vertical flow (or dipstick) devices, the assay device is inserted (e.g., "dipped") into a sample within a container and the sample wicked up the test strip to provide a test result. An example of such a device is the QuickVue® Influenza A+B (Quidel Corp., San Diego, Calif.). An exemplary assay device employing lateral flow is the QuickVue® One-Step hCG Combo Test (Quidel Corp., San Diego, Calif.).

As used herein, the term "identifying a defect" refers to finding, revealing, discovering, or determining the existence of a flaw or imperfection in a part or assembly. The flaw or imperfection may be critical to the function of the part or assembly, or may be cosmetic. Examples of flaws or imperfections include but are not limited to imperfect castings or moldings, improper assembly, missing or incomplete components, misalignment of parts, process residues, external contamination, and the like. The identification may be performed visually; using a high speed camera; by measuring an output, critical dimension or parameter of the part or assembly, for example, optical density; by measuring the mass of a part of assembly; or by any other means that allows a defective part to be distinguished from a correct (i.e., non-defective) part.

As used herein, "marking" refers to applying a distinguishing feature, e.g., for distinguishing a defective part or assembly from a non-defective part or assembly. In preferred embodiments, the mark is produced by applying magnetic ink to the defective parts or assembly, e.g., in the form of a line, squiggle, scribble, dot, smear, or other mark.

As used herein, "magnetic ink" is a magnetically detectable ink, such as that used to print the Magnetic Ink Character Recognition (MICR) characters that encode account numbers on bank checks. Magnetic ink includes ferrofluids, which are generally comprised of microscopic ferromagnetic nano-particles (e.g., magnetite, hematite or some other compound containing $Fe^{2+}$ or $Fe^{3+}$ atoms). Ferrofluids may contain surfactants, such as oleic acid, tetramethylammonium hydroxide, citric acid, soy lecithin, etc. to reduce agglomeration. Most ferrofluids are actually paramagnetic, i.e., they become magnetic only in response to a magnetic field. Both true ferromagnetic fluids and paramagnetic fluids may be used according to the present methods. The presence of magnetic ink can be determined using a magnetic checker, which is a standard device known in the art. Magnetic fluid was first described by Albrecht, T. et al. (1985) *Applied Physics A: Materials Science & Processing* 65:215-220).

As used herein, "isolating the defective part or assembly," or similar expressions refers to segregating or separating a defective part or assembly from non-defective parts or assemblies, or isolating a product containing a defective part or assembly from products containing non-defective parts or assemblies. Isolation may be performed at any time following the detection of the defective part or assembly, preferably at a convenient time following the completion of a continuous manufacturing process or step, thereby minimizing the down time required to isolate defective parts or assemblies. Isolated defective parts or assemblies may be discarded or further examined to better understand the nature of the defect and/or prevent or minimize its/their occurrence.

II. Overview

The present methods are for detecting a defective part or assembly in a manufactured product. The methods are particularly useful for detecting a defective part or assembly in an intermediate or final product obtained from a continuous manufacturing process, in which the defective part or product is concealed or obscured. This problem frequently arises when parts or assemblies made by a continuous manufacturing process are assembled into larger components, where they are no longer accessible for inspection or removal.

In particular, the present methods provide that a defective part or assembly identified during manufacturing, is marked with magnetic ink, which can be detected at a convenient time following manufacturing. The magnetic ink can be detected even if the marked defective part or assembly is concealed, hidden, obscured, or otherwise inaccessible to conventional methods of detection.

Preferred embodiments of the methods are described, below. Further embodiments will be apparent from the description.

III. Methods for Detecting Defects in Parts and Assemblies

Detection of defective product on an assembly line or related manufacturing scheme is typically performed by a class of instruments known as "defect scanners." These instruments automatically scan surfaces and record the location of defects using a microprocessor device, which produces a "defect map" for use by a manual or automatic defect review station, where defective parts or assemblies (or products containing the same) are detected and discarded.

Scanners are usually optical devices, including but not limited charge-coupled device (CCD) cameras and complementary metal oxide semiconductor (CMOS) sensors. These technologies are widely used in imaging devices, such as, digital still and video cameras, optical scanners, facsimile machines, and robotics. Scanners may use conventional incoherent light sources like filament lamps and gas discharge lamps, or coherent light sources, such as short wavelength lasers. Examples of inspection methods, as well as apparatus and circuitry for implementing these methods, are described in various U.S. patents, including, inter alia, U.S. Pat. Nos. 4,247,203, 4,532,650, 4,579,455, 4,805,123, 4,926,489, 5,619,429, 5,864,394, 5,699,447, 5,825,482, 7,133,548, and 6,952,491. The disclosures of these patents are incorporated herein by reference.

IV. Methods of Marking Defective Darts and Assemblies

Following the identification of defects with the scanner, magnetic ink is applied to defective parts or assemblies to facilitate their detection following manufacturing. Magnetic ink may be applied by conventional application methods such as brushing, spraying, and roll coating, as well as by printing methods, including conventional contact printing, air-atomized spraying, air-assisted spraying, airless spraying, high-volume low-pressure spraying, air-assisted airless spraying, continuous ink jet printing, binary printing, and laser printing, all of which are known in the art. A sufficient amount of magnetic fluid is applied to allow the detection of a defective assembly, even if hidden, concealed, or inaccessible in a final or intermediate product of a manufacturing procedure.

Magnetic ink includes ferrofluids, which generally contain microscopic ferromagnetic nano-particles (e.g., magnetite, hematite or another compound containing $Fe^{2+}$ or $Fe^{3+}$ atoms). The magnetic material is typically suspended in a liquid carrier, optionally in combination with dispersing agents, surfactants, pigments, binder resins, plasticizers, flexibilizers, weatherability improvers, and fillers, to form a colloidal magnetic fluid, which may be is referred to as a ferrofluid.

The liquid carrier may be a non-aqueous solvent, including (i) non-polar solvents such as aliphatic hydrocarbons, e.g., heptane, decane, mineral oil, kerosene, and the like; (ii) halogenated hydrocarbons, e.g., carbon tetrachloride, trichloroethylene and the like; and (iii) aromatic solvents, e.g., benzene, toluene and the like. The liquid carrier may also be an aqueous solvent, optionally with a small amount of organic solvent. Surfactants may be added to increase the solubility of one or more components in the magnetic ink, and/or to reduce agglomeration. Surfactants include oleic acid, tetramethylammonium hydroxide, citric acid, soy lecithin, etc.

Organic liquid carriers for ferrofluids are described in, e.g., U.S. Pat. Nos. 4,430,239, 4,416,751, 4,604,222, 4,687,596, 4,732,706, 4,867,910, and 5,085,789. Aqueous carrier fluids are described in, e.g., U.S. Pat. Nos. 3,990,981, 4,416,751, 5,240,626, and 5,843,579.

Most ferrofluids are actually paramagnetic, i.e., they become magnetic only in response to a magnetic field. True magnetic ferrofluids tend to be less stable. Both true ferromagnetic fluids and paramagnetic fluids may be used according to the present methods.

V. Methods of Detecting Magnetic Ink

Magnetic ink can be detected using a magnetic sensor (or checker), which is a standard device known in the art. Such sensors typically contain a Hall element, a magnetoresistive (MR) element, a giant magnetoresistive (GMR) element, and/or a fluxgate element. Exemplary magnetic sensors are described in, e.g., U.S. Pat. Nos. 4,518,919, 4,639,807, 4,709, 208, 4,988,850, 5,201,395, and 6,323,634.

The magnetic sensor is used to detect magnetic ink marked on a defective part or assembly that is incorporated into a final or intermediate product from a manufacturing process. Magnetic sensors may be positioned along the path traveled by parts or assemblies during manufacturing, such that defective parts or assemblies are automatically detected. In one example, defective parts and assemblies are detected at the end of a continuous manufacturing process, such as a reel-to-reel process.

Alternatively, magnetic ink markings on defective parts may be detected manually, e.g., using a hand-held or similar magnetic sensor.

VI. Methods of Isolating Defective Parts or Assemblies

Methods for isolating defect parts or assemblies include processes collectively known as defect review. Defect review is conventionally performed manually or automatically, using a defect map as described above. In the case of limited quantities of products and/or complex review requirements, manual review may be preferred.

Automatic defect characterization (ADC) is well known in semiconductor and microprocessor manufacturing, where conventional, white-light-microscope-based review stations have been replaced by an ADC system that automatically loads each suspected-defective wafer based on the defect map, captures a digital image of the relevant portion of the wafer, and in some cases, further characterize the defect. In fully automated systems, the defective part or assembly is physically isolated from the non-defective parts for disposal or further analysis. In cases where the product value is low and/or the throughput is high, defect maps can be used to immediately isolate defective parts or assemblies without further review.

In the case of the present methods, defect review may be performed by detecting magnetic ink in the final or intermediate products of a manufacturing process, and then physically isolating the defective parts or assemblies for disposal or further analysis. Alternatively, data relating to the location of magnetic ink-containing defective parts or assemblies may be used to prepare a defect map for later isolating defective parts or assemblies. A conventional defect map, i.e., prepared using data obtained from a scanner, may be used in combination with a magnetic sensor to track or locate defective products or assemblies (or final or intermediate products containing such defective products or assemblies). However, a conventional defect map is not required for use in combination with a magnetic sensor, since the use of magnetic ink allows the detection of the defective part or assembly directly, without relying on a conventional defect map prepared by a scanner.

VII. Advantages of the Present Methods

The present methods allow the detection of a marked defective part or assembly, even if the part or assembly is completely or partially concealed, hidden, or buried within the final or intermediate product of a continuous manufacturing process. Prior to this method, such defective parts or assemblies would have to be (i) detected and isolated while they were accessible, i.e., before being assembled into a final (or intermediate) product or (ii) identified while accessible, and then later correlated with a final or intermediate product using, e.g., a defect map. In the first case, the need to leave defective parts or assemblies accessible at the end of a continuous manufacturing process limits the number of steps that can be performed in a continuous and substantially uninterrupted manner. In the second case, the isolation of a final or intermediate product containing defective parts or assemblies relies on the accuracy of a defect map prepared from scanner data, in combination with a dependable indexing system to ensure that defective parts or assemblies can later be found and isolated.

The ability to detect defective, concealed, or hidden defective parts means that more manufacturing steps can be performed before it is necessary to interrupt the manufacturing process to detect and isolate defective parts or assemblies or products containing the same. The ability to detect defective parts and assemblies using a magnetic sensor also eliminates the reliance on defect maps and indexing mechanisms. Using magnetic ink, defective parts and assemblies can be identified even if a defect map is lost or the indexing system fails.

The present methods are useful for detecting defects in most any assembly-line based manufacturing process, where it is undesirable to interrupt the manufacturing process to isolate defective parts or assemblies. Assembly-line based manufacturing processes include reel-to-reel manufacturing, which is widely used in the semiconductor and integrated circuit (IC) industry as well as useful in the manufacture of assay devices, particularly laminated test strip-based, lateral (or vertical) flow assay devices.

An exemplary use of the present methods is for detecting defective microfluidic circuits, for example, in parts or assemblies built up from layers of material. In a particular example, a scanner (e.g., a high-speed camera) identifies defects in material layers, which result in improperly dimensioned passages or capillaries (or other defects) within a part or assembly of a microfluidic device. The part or assembly is marked with magnetic ink for later detection by a magnetic sensor, at which time the defective part or assembly (or final product containing the same) is isolated for further analysis or simply discarded. The use of magnetic ink allows the defect to be detected even if the defective layers are concealed or hidden, e.g., by additional layers that are applied during the same continuous manufacturing process.

A further exemplary use of the present methods is for detecting a defective component of a laminated test strip-based assay device, such as a lateral flow or vertical (dipstick-type) immunoassay device. Such devices are well known in the art, see for example, Lambotte, et al., U.S. Pat. No. 7,179,657, Boehringer, et al., U.S. Pat. No. 7,144,742, Pronovost, et al., U.S. Pat. No. 6,656,744 and Lambotte, et al., WO2005/031355, each of which is hereby incorporated by reference in its entirety, as well as commercially available rapid diagnostic devices such as the QuickVue® Influenza A+B (Quidel Corp., San Diego, Calif.) and QuickVue(D One-Step hCG Combo Test (Quidel Corp., San Diego, Calif.).

Laminated test strip-based assay devices may be manufactured by manual assembly, but are preferably manufactured using an automated continuous manufacturing process such as reel-to-reel manufacturing. When manufactured in an exemplary automated continuous process, a component material is unwound from one reel, reagents are applied (for example, via printing, spraying or the like) to the component material in desired quantities and at desired locations on the material, and once manipulation of the material is completed, the component material is rewound onto another reel. Reels of different component materials are then assembled, via an automated continuous process, into test strips, such that components overlap with one another and/or comprise opaque materials covering one or more surfaces of such components. Completed test strips may additionally be automatically placed into an opaque or partially opaque housing and/or packaged into opaque packaging.

Along the continuous manufacturing process, inspection points are established, for example, by placement of scanner, camera or other optical device along with and in communication with means for applying a magnetic-ink mark, within the line of assembly. Such inspection points permit in-line identification of defective components and, further, marking of such defective component with said magnetic-ink. Such defective part is then identified and segregated from non-defective parts at a convenient point in the manufacturing process including, without limitation, after completion of manufacturing.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A method for detecting a defective component in a laminated device which is a final or intermediate product of a continuous manufacturing process which employs an assembly line, the method comprising:
a) identifying a defect in said defective component during said continuous manufacturing process, by means of a scanning device placed at one of a plurality of inspection points within the assembly line, wherein each said inspection point comprises such a scanning device in communication with means for applying magnetic ink;
b) marking the defective component with said magnetic ink during said continuous manufacturing process;
c) detecting the magnetic ink in said final or intermediate product containing the defective component; and
d) isolating the final or intermediate product in which said magnetic ink is detected, said product containing the defective component,
wherein said magnetic ink is substantially concealed in said final or intermediate product,
and wherein said defect is in a layer of said laminated device which is substantially concealed in said final or intermediate product, due to lamination of components.

2. The method of claim 1, wherein the final or intermediate product is a laminated microfluidic device, and the defect is a defective capillary within the microfluidic device.

3. The method of claim 1, wherein the manufacturing process comprises a reel-to-reel process.

4. The method of claim 3, wherein the defect is identified using a camera to visually inspect the defective component during the manufacturing process.

5. The method of claim 1, wherein the marking is performed by spraying magnetic ink on the defective component.

6. The method of claim 1, wherein the marking is performed by spotting magnetic ink on the defective component.

7. The method of claim 1, wherein the final or intermediate product is an assay device.

8. The method of claim 7, wherein the assay device is a laminated test strip-based assay device.

* * * * *